United States Patent [19]

Jackson

[11] Patent Number: 5,476,478
[45] Date of Patent: Dec. 19, 1995

[54] PREOPERATIVE SKIN STRETCHING APPARATUS AND METHOD

[75] Inventor: Ian T. Jackson, Bloomfield Hills, Mich.

[73] Assignee: Providence Hospital, Southfield, Mich.

[21] Appl. No.: 228,667

[22] Filed: Apr. 18, 1994

[51] Int. Cl.⁶ .................................................. A61F 5/00
[52] U.S. Cl. ................................. 606/204.35; 128/898
[58] Field of Search ..................... 606/204.35, 204.45, 606/131–132; 128/898, 774; 602/17, 74–75; 607/109; 623/66

[56] References Cited

U.S. PATENT DOCUMENTS

| | | | |
|---|---|---|---|
| 1,510,879 | 10/1924 | Yachno | 606/204.35 |
| 2,575,204 | 11/1951 | Brown . | |
| 2,575,205 | 11/1951 | Brown . | |
| 2,619,084 | 11/1952 | Brown . | |
| 3,575,165 | 4/1971 | Heale | 606/204.35 |
| 3,654,914 | 4/1972 | Franklyn | 128/898 X |
| 3,672,363 | 6/1972 | Masters . | |
| 3,731,677 | 5/1973 | Salvati | 606/204.35 |
| 3,736,925 | 6/1973 | Erman . | |
| 3,782,372 | 1/1974 | Carlton | 606/204.35 |
| 4,239,037 | 12/1980 | Fausone | 606/204.35 |
| 4,896,680 | 1/1990 | Hirshowitz . | |
| 4,955,395 | 5/1990 | Mandero . | |
| 4,957,480 | 9/1990 | Morenings . | |
| 4,995,379 | 2/1991 | Brooks . | |
| 5,067,482 | 11/1991 | Reid | 606/204.35 |
| 5,127,412 | 7/1991 | Cosmetto et al. . | |

OTHER PUBLICATIONS

Bernard Hirshowitz, F.R.S.C., Ella Lindenbaum, Ph.D., Yaron Har–Shai, M.D., A Skin Stretching Device (SSD) for the Harnessing of the Visco–Elastic Properties of the Skin.

B. Hirshowitz, F.R.S.C., Ian T. Jackson, An Attempt to Harness the Visco–Elastic Properties of the Skin in Face Lift Operations—A Preliminary Report, Annals of Plastic Surgery, vol. 18, No. 3, Mar. 1987, pp. 188–198.

Life Medical Sciences, Inc., Sure–Closure Skin Stretching System, Technical Bulletin No. 1.

Primary Examiner—Linda C. Dvorak
Attorney, Agent, or Firm—Basile and Hanlon

[57] ABSTRACT

A preoperative skin stretching apparatus and method for preoperatively stretching facial and neck skin to alleviate the complications associated with the extensive undermining of the soft tissues of the face and neck that occur when performing facelifts. The preoperative skin stretching apparatus utilizes a plurality of skin attachments that are sutured superficially to predetermined areas of the skin. A nondistensible headcap is fitted onto a patient's head and covers the rear of the neck and the posterior, superior and frontal areas of the head. A plurality of straps are fixedly attached to the headcap and extend through rectangular apertures provided in the skin attachments. The free end of the straps are pulled rearward toward the headcap in order to pull the skin attachments rearward and apply tension to the skin. The material cooperatively engages to detachably and adjustably maintain the position of the skin attachments and the tension on the skin. Once the skin has stretched, the material on the straps is disengaged, and the free end of the straps is pulled further rearward, along with the skin attachments, to obtain the tension on the skin that was originally applied. After the skin has stretched a desired amount, the headcap and skin attachments are removed, and the facelift procedure is completed.

7 Claims, 1 Drawing Sheet

PREOPERATIVE SKIN STRETCHING APPARATUS AND METHOD

FIELD OF THE INVENTION

The present invention relates to the preoperative stretching of skin, and more particularly, to a method and apparatus for preoperatively stretching facial and neck skin in order to alleviate the complications associated with the extensive undermining of the soft tissues of the face and neck that occur when performing facelifts.

BACKGROUND OF THE INVENTION

Societies' desire to obtain a more youthful appearance has increased the demand for rejuvenation surgery. Many techniques have been developed attempting to improve aesthetic results and prolong the operative improvement. These techniques require extensive dissection not only of the skin and superficial facial layers but also the superficial musculoaponeurotic system. Thus, the duration of the operation and risk of complications, such as anesthesia of the ear, hematomas, facial nerve deficit, skin slough, infection and hair loss, increases dramatically.

One of the more common rejuvenation surgeries is the rhytidectomy procedure or facelift surgery. In facelift surgery, the soft tissues of the face and neck are widely undermined allowing for advancement of the facial and neck flap upward and backward. Again, such extensive undermining of the soft tissues of the neck and face may lead to complications such as hematoma, risk of facial nerve injury and skin loss.

Many have attempted to harness the viscoelastic properties of skin in order to maximize the amount of neck and facial skin excised and avoid the extensive undermining of the skin by stretching or expanding the skin intra-operatively. Such viscoelastic properties allow skin to stretch to a certain extent, but by virtue of creep, the skin will stretch further under the same load over a period of time. Unfortunately, intra-operative procedures limit the amount of time in which the skin may be allowed to stretch. If the skin is not allowed to stretch enough, the tension applied to the skin after completion of the facelift procedure may lead to the skin stretching by virtue of creep, thereby diminishing the aesthetic results of the facelift procedure.

Few intra-operative skin stretching techniques have been developed for preoperative use, but one skin stretching technique that has been utilized for preoperative use is the silicone bag expansion procedure or tissue expansion procedure wherein in the intra-operative procedure, a silicone bag is surgically implanted in a deflated position underneath the skin. The bag is then inflated with a saline solution in order to provide tension on the skin. After the skin has been allowed to stretch, the bag is deflated and removed, and the excess skin is then excised.

The tissue expander or silicone bag has been used preoperatively for tumor surgeries wherein the device is implanted in a surgical pocket, adjacent to the tumor, and incrementally inflated. Weeks later, the device is removed during the second procedure in which the tumor is excised. The additional expanded tissue is used to close the large defect created by the tumors absence. Two separate surgical procedures are required.

The inflatable tissue expander is associated with many complications arising from the additional surgical trauma required for creation of its deep subcutaneous pocket. The device itself is easily punctured, may leak or otherwise mechanically fail, appears cosmetically deforming when inflated, and most importantly, may destroy the overlying skin by pressure necrosis because there are no means of measuring the tension on the skin as a safeguard against over inflation. Also, in facelift operations, the optimal direction of traction for achieving the intended effect is upward and backward. A drawback, therefore, with an expansion device placed under the skin for rapid expansion is that the skin is stretched multiaxially. As a result, there is some dissipation of the stretching force because many collagen fibers, the fibers in the skin that allow the skin to stretch, are stretched in an unfavorable direction.

As previously stated, intra-operative procedures do not provide an ample amount of time to completely take advantage of the viscoelastic properties that allow the skin to stretch over a period of time. Also, the procedures do not maintain a constant tension or provide a reestablishment of the tension on the skin once the skin is stretched in response to the tensioning force. Therefore, it would be desirable to provide a preoperative apparatus and method for stretching the facial and neck skin prior to facelift surgery in order to maximize the amount of skin excised and alleviate the complications associated with the extensive undermining of the soft tissues of the neck and facial skin that occur when performing facelifts.

SUMMARY OF THE INVENTION

The present invention provides a preoperative skin stretching apparatus and method that alleviates the complications associated with extensive undermining of the skin that occurs when performing facelifts by first stretching the facial and neck skin with elastic traction an ample amount of time prior to the facelift procedure. The preoperative skin stretching apparatus provides for a headcap made of a nondistensible material which fits over a rear portion of the neck and rear and top portions of the head of a patient. A plurality of adjustable straps are fixedly connected to and extend from the headcap. A plurality of skin attachments are secured to predetermined areas of the neck and facial skin. The straps extend through an aperture provided in the skin attachments to provide a detachable and adjustable coupling means between the headcap and the skin attachments. A free end of the straps are pulled rearwardly thus pulling the skin attachments rearward, until the proper tension is applied to the skin. The strap material cooperatively engage to form a detachable connection for maintaining the position of the skin attachments and the tension of the skin.

The preoperative skin stretching method utilized to alleviate the complications associated with the extensive undermining of the neck and facial skin that occurs when performing a facelift involves first determining the proper areas of the skin that should be pulled. The skin attachments are sutured superficially to the predetermined pull areas of the skin, and the headcap is then fitted on the head of the patient. The straps are inserted through the aperture provided in the skin attachments, and the free end of the straps are pulled rearward, along with the skin attachments, until the proper tension is provided on the skin. Opposite sides of the strap material are brought together for cooperative engagement in order to maintain the position of the skin attachments thus maintaining the tension on the skin. The skin is allowed to stretch, and after the skin has stretched and the tension has dissipated, the straps are disengaged, and the free end of the straps are pulled further rearward, along with the skin attachments, to reestablish the proper tension on the skin.

Again, the skin is allowed to stretch, and the cycle is repeated a plurality of times until the skin has stretched a desired amount. The headcap and skin attachments are removed, and the facelift procedure is completed.

To this end, the object of the present invention is to provide a new and improved preoperative skin stretching apparatus and method that avoids the complications associated with the extensive undermining of skin during facelift procedures by first stretching the facial and neck skin with elastic traction an ample amount of time prior to the facelift procedure.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
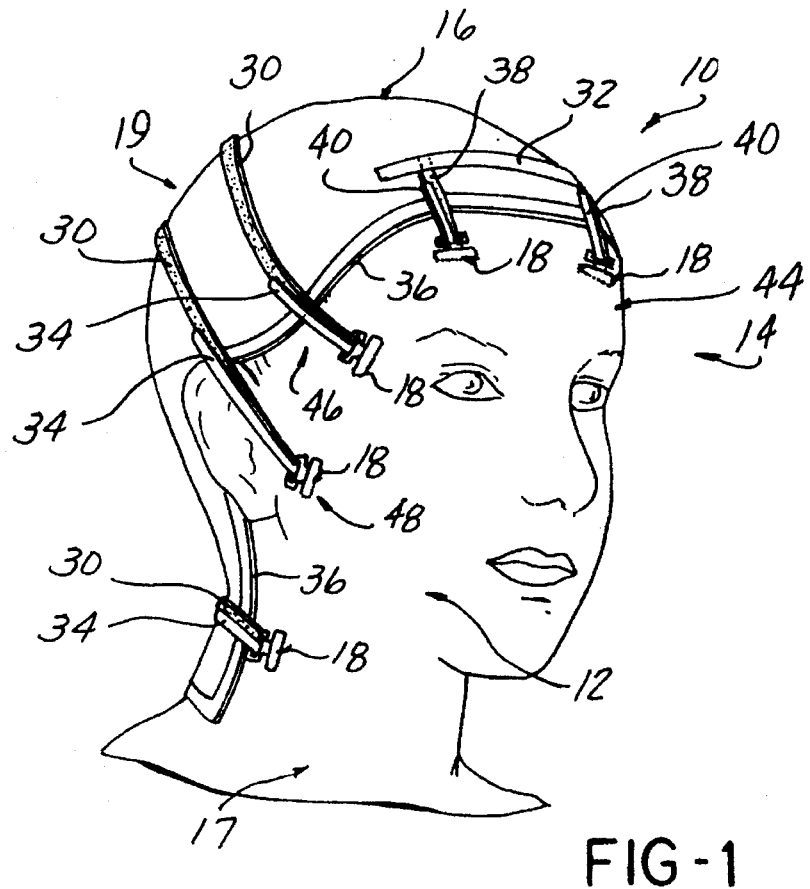
FIG. 1 is a perspective view of the preoperative skin stretching apparatus being utilized on a patient prior to facelift surgery.

FIG. 1 shows a preoperative skin stretching apparatus 10 of the present invention being utilized to stretch the neck and facial skin 12 of a patient 14 prior to facelift surgery. The skin stretching apparatus 10 utilizes a headcap 16 extending over the rear portions of the neck 17 and the head 19 of the patient 14. A plurality of non-elastic coupling means are fixedly connected to the headcap 16. A plurality of retaining means are connected to predetermined areas of the skin 12, and the coupling means detachably and adjustably couples the retaining means to the headcap 16 to maintain the predetermined areas of the skin 12 in a rearward position thus maintaining a desired tension on the skin 12. Once the skin 12 stretches a desired amount, the headcap 16 and retaining means are removed, and the facelift procedure is completed.

Figure 2:
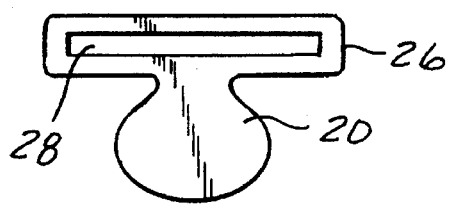
FIG. 2 is a perspective view of the bracket portion and the tab portion of the skin attachment.
Figure 3:
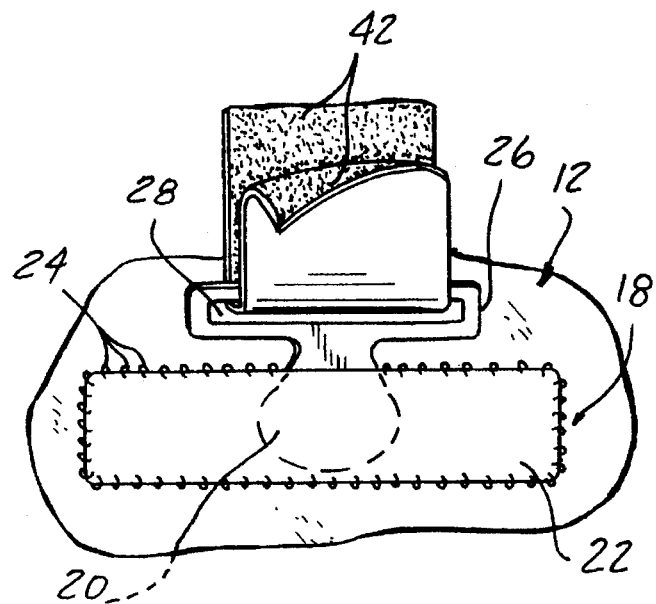
FIG. 3 is a perspective view showing the skin attachment sutured superficially to the skin and coupled with the velcro strap.

In order to stretch the skin 12 preoperatively, a surgeon (not shown) predetermines what areas of the skin 12 to pull, and a plurality of skin attachments 18 are fixedly connected to the predetermined areas of the skin 12 in order to retain the skin 12 when pulled. As best seen in FIGS. 2 and 3, each skin attachment 18 has a tab portion 20 that is substantially flat and circular. The tab portion 20 may be sewn to a flexible material 22, such as cloth, although a conventional adhesive (not shown) may also be utilized to connect the tab portion 20 to the flexible material 22. The flexible material 22 is sutured superficially to the predetermined areas of the skin 12 wherein a non-absorbable suture material 24 is utilized to ensure that the sutures 24 do not weaken over time. A substantially rectangular and flat bracket portion 26 is integral with and extends from the tab portion 20 and has a substantially rectangular aperture 28 extending therethrough.

To provide a good base from which the skin 12 may be pulled, the headcap 16 extends over the back of the neck 17 and the posterior, superior and upper frontal area of the head 19, as seen in FIG. 1. The headcap 16 is properly fitted to provide a snug fit on the patient's head 19. The headcap 16 is fabricated from a lightweight, comfortable, compact, nondistensible material such as a fine, stiff mesh. The nondistensiblity of the headcap 16 prevents the headcap 16 from stretching when subjected to forces pulling the skin attachments 18.

The headcap 16 has four strips 30, 32 of nondistensible, non-elastic material connected thereto with three 30 of the four strips 30, 32 extending circumferentially around the rear of the headcap 16, and the fourth strip 32 extending laterally, substantially parallel to the top frontal edge of the headcap 16. The three circumferential strips 30 are fixedly connected to the headcap 16 while also having free ends 34 that extend beyond the periphery 36 of the headcap 16. The fourth strip 32 has a pair of substantially parallel strips 38 that extend substantially perpendicular therefrom and which also have free ends 40 extending beyond the periphery 36 of the headcap 16. The free ends 34, 40 of the strips 30, 38, respectively, extend through the apertures 28 provided in the bracket portions 26 of the skin attachments 18, and the free ends 34, 40 of the strips 30, 38 double back to overlie the portion of the strips 30, 38 extending between the skin attachments 18 and the periphery 36 of the headcap and continue to overlie the portion connected to the headcap 16. The opposing sides of the strips 30, 38 have a multiplicity of anchor-type hooks fixedly attached on one side of the strips 30, 38 and adapted to engage a layer of felt like fibers on the other side of the strips 30, 38. Material of this type is presently available from at least one manufacturer under the trade name "VELCRO". The "VELCRO" material 42 cooperatively engages to retain the skin attachments 18 in a desired rearward position, towards the headcap 16, in order to maintain a certain level of tension on the skin 12. The "VELCRO" material 42 provides for simple detachment and adjustment of the skin attachments 18 and the tension applied to the skin 12.

To preoperatively stretch the skin 12 before a facelift procedure, the surgeon determines the areas of the neck and facial skin 12 that are to be pulled in order to properly stretch the skin 12. Such areas of the skin 12 are typically along the forehead 44, the temporal area 46, the cheek 48 and the neck 17 of the patient 14. The flexible material 22 of the skin attachment 18 is sutured superficially to the predetermined areas of the skin 12 using the nonabsorbable suture material 24. This can be done under a local anesthetic. Once the skin attachments 18 are secured to the desired areas of the skin 12, the headcap 16 is fitted onto the patient's head 19. The free ends 34, 40 of the strips 30, 38, respectively, are inserted through the corresponding apertures 28 in the bracket portions 26 of the skin attachments 18. The free ends 34, 40 of the strips 30, 38 are pulled rearward so as to pull the skin attachments 18 rearward toward the headcap 16 in order to provide tension to the neck and facial skin 12. Once the proper tension on the skin 12 is obtained, the strips 30, 38 are brought together to cooperatively engage the "VELCRO" material 42 and maintain the position of the skin attachments 18 and the tension on the skin 12. The skin 12 is then allowed to stretch.

Once the skin 12 begins to stretch and the skin 12 begins to accumulate in the area between the skin attachments 18 and the headcap 16, the tension on the skin 12 begins to dissipate. At this time, the "VELCRO" material 42 on the strips 30, 38 is disengaged, and the free ends 34, 40 of the strips 30, 38 are pulled further rearward along with the skin attachments 18, to increase the tension on the skin 12 to the level of tension that was originally applied. The "VELCRO" material 42 of the strips 30, 38 are brought together to cooperatively engage and maintain the more rearward position of the skin attachments 18 and the renewed tension level. This process is continued a plurality of times, approximately 48 to 72 hours, until the skin 12 has stretched a desired amount. The headcap 16 and skin attachments 18 are removed, and the facelift procedure may begin.

It should be noted that the present invention is not limited to preoperative stretching of only facial and neck skin, but rather, the present invention may be utilized to stretch any area of skin preoperatively where it would be an advantage to do so. Also, the present invention is not limited to being utilized in conjunction with facelift procedures, but rather, the present invention may be used in conjunction with any surgical procedure wherein preoperative stretching of skin would be beneficial.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for preoperatively stretching skin prior to a facelift, the steps comprising:
    (a) suturing skin attachments to predetermined areas of the skin;
    (b) fitting a nondispensible headcap on the head of the patient wherein said headcap has a plurality of adjustable straps attached thereto and extending therefrom;
    (c) adjustably and detachably coupling said straps to said skin attachments to retain said skin attachments in a rearward position toward said headcap and provide a desired tension on said skin; and
    (d) allowing for the skin to stretch prior to conducting a surgical facelift.

2. The method stated in claim 1 including the steps comprising:
    (e) adjusting the coupling of said straps and said skin attachments to move said skin attachments further rearward toward said headcap to maintain tension on the skin after allowing the skin to stretch.

3. The method stated in claim 2 including repeating each of the steps (e) and (d) a plurality of times until the skin has stretched a desired amount.

4. A method for preoperatively stretching skin prior to a facelift, the steps comprising:
    (a) selecting areas of the skin to be pulled;
    (b) suturing skin attachments superficially to said selected areas of the skin wherein a bracket portion of said skin attachments has an aperture extending therethrough;
    (c) fitting a nondispensible headcap on the head of the patient wherein said headcap has a plurality of adjustable straps attached thereto and extending therefrom;
    (d) inserting a free end of said straps through said aperture of said bracket portion of said skin attachment and back toward said headcap;
    (e) pulling said free end of said straps rearward toward said headcap along with said skin attachments until a desired tension is placed on the skin;
    (f) cooperatively engaging said straps to retain said skin attachments in a rearward position toward said headcap to adjustably maintain tension on the skin; and
    (g) allowing the skin to stretch prior to conducting a surgical facelift.

5. The method stated in claim 4 including the steps comprising:
    (h) disengaging said straps after the skin has stretched; and
    repeating each of said steps (e), (f) and (g).

6. The method stated in claim 5 including repeating each of the steps (h), (e), (f) and (g) a plurality of times until the skin stretches a desired amount.

7. A method for preoperatively stretching skin prior to a facelift, the steps comprising:
    (a) suturing skin attachments superficially to predetermined areas of the skin;
    (b) fitting a nondispensible headcap on the head of a patient for adjustably retaining said skin attachments;
    (c) pulling said skin attachments rearward toward said headcap and attaching them thereto until a desired tension is placed on the skin; and
    (d) allowing the skin to stretch prior to performing a surgical facelift.

* * * * *

UNITED STATES PATENT AND TRADEMARK OFFICE
CERTIFICATE OF CORRECTION

PATENT NO. : 5,476,478
DATED : December 19, 1995
INVENTOR(S) : Ian T. Jackson

It is certified that error appears in the above-indentified patent and that said Letters Patent is hereby corrected as shown below:

Column 5, line 36, delete "nondispensible" and insert --nondistensible--.

Column 6, line 12, delete "nondispensible" and insert --nondistensible.--

Column 6, line 39, delete "nondispensible" and insert --nondistensible--.

Signed and Sealed this

Fourteenth Day of May, 1996

Attest:

BRUCE LEHMAN

*Attesting Officer*  *Commissioner of Patents and Trademarks*

UNITED STATES PATENT AND TRADEMARK OFFICE
Certificate

Patent No. 5,476,478                                                              Patented: December 19, 1995

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ian T. Jackson, Bloomfield Hills, MI; and Rick Joel Smith, East Lansing, MI.

Signed and Sealed this Twenty-fourth Day of February 2004.

LINDA C. M. DVORAK
*Supervisory Patent Examiner*
Art Unit 3739